United States Patent [19]

Hemler et al.

[11] Patent Number: 5,583,203
[45] Date of Patent: Dec. 10, 1996

[54] VLA PROTEINS

[75] Inventors: Martin E. Hemler, Auburndale; Yoshikazu Takada, Brookline, both of Mass.

[73] Assignee: Dana-Farber Cancer Institute, Boston, Mass.

[21] Appl. No.: 400,465

[22] Filed: Mar. 7, 1995

Related U.S. Application Data

[63] Continuation of Ser. No. 927,864, Aug. 10, 1992, abandoned, which is a continuation of Ser. No. 799,708, Nov. 26, 1991, abandoned, which is a continuation of Ser. No. 160,887, Feb. 26, 1988, abandoned.

[51] Int. Cl.$^6$ .................... C07K 14/725; C07K 14/78; C07K 16/28
[52] U.S. Cl. .................... 530/395; 530/350; 530/388.2; 530/388.22; 530/388.73; 530/388.75
[58] Field of Search .................... 330/350, 395, 330/388.73, 388.75, 806; 530/350, 395, 387, 388.2, 388.22, 388.73, 388.75

[56] References Cited

PUBLICATIONS

Hemler, et al., J. Immunol. 131:334 (1983).
Hemler, et al., J. Immunol. 132:3011 (1984).
Sanchez–Madrid, et al., Eur. J. Immunol. 15:502 (1985).
Hemler, et al., J. Biol. Chem. 260:15246 (1985).
Hemler, et al., J. Clin. Invest. 78:696 (1986).
Hemler, et al., J. Biol. Chem. 262:3300 (1987) Report.
Takada, et al., Nature, 326:607 (1987).
Hemler, et al., *J. Biol. Chem.* vol. 263, No. 16, pp. 7660–7665 (1988).
Y. Takada, Chemical Abstract, 110:73524y pp. 73520, (1989).
Takada, et al., *J. of Cell. Biochem.*, 37:385 (1988).
Sanchez–Madrid, et al., *Eur. J. Immunol.* 16:1343 (1986).
Takada, et al., *Proc. Natl. Acad. Sci. USA*, 84:3239 (1987).
Hemler, et al., *J. of Biol. Chem.*, vol. 262, No. 24, pp. 11478–11485 (1987).
Puliolo et al. 1991. J. Biol. Chem. 266:10241–10245.
Clayberger et al. 1987. (Mar. 1) J. Immunol. 138 (5) 1510–1514.
Bednarczyk et al. 1990. J. Immunol. 144(3):777–784.
Elicer et al. 1990 Cell 60:577–584.
Wayner et al. 1989 J. Cell Biology 109:1321–1330.

*Primary Examiner*—Robert A. Wax
*Assistant Examiner*—G. E. Bugaisky
*Attorney, Agent, or Firm*—David G. Conlin; Ronald I. Eisenstein

[57] ABSTRACT

Three new and distinct heterodimers in the very late antigen (VLA) protein family are disclosed, namely VLA-3, VLA-4 and VLA-5, as well as monoclonal antibodies therefor. The N-terminal amino acid sequence for each of the VLA α subunits is also disclosed.

11 Claims, No Drawings

VLA PROTEINS

This is a continuation of application Ser. No. 07/927,864 filed on Aug. 10. 1992, which is a continuation of U.S. Ser. No. 07/799,708, filed Nov. 26, 1991, which is a continuation of U.S. Ser. No. 07/160,887, filed Feb. 26, 1988, all now abandoned.

BACKGROUND OF THE INVENTION

This invention relates to a very late antigen (VLA) protein family isolated from human cell tissue which has extracellular matrix adhesion function.

Human very late antigen (VLA) heterodimers VLA-1 and VLA-2 have been disclosed by Hemler et al (*J. Immunol.* 131:334, 1983; *J. Immunol.* 132:3011, 1984; *Eur. J. Immunol.* 15: 502, 1985; *J. Biol. Chem.* 260:15246, 1985; *J. Clin. Invest.* 78:696, 1986). These are separate protein complexes of $M_r$ 210,000/130,000 and $M_r$ 165,000/130,000, respectively, which share a common β subunit of $M_r$ 130,000, but have unique α subunits. Both VLA-1 and VLA-2 appear very late after T cell activation and varying amounts of VLA-1 relative to VLA-2 are obtained during long term T cell culture. A monoclonal antibody for VIA-1, from murine hybridoma TS2/7, is sold by T Cell Sciences, Inc. for identification of long term or chronically activated *T lymphocytes* and thymocytes, and assessment of human T-cell function, particularly in response to antigenic and mitogenic stimuli. Detection of VLA-1 is also used for correlation and assessment of chronic autoimmune diseases, such as multiple sclerosis, systemic lupus erythematous, and rheumatoid arthritis, as well as chronic viral infections. For example, increases in VLA-1 expression have been observed on the surface of T-cells of active multiple sclerosis patients.

SUMMARY OP THE INVENTION

It has now been discovered that the very late antigen (VLA) protein family contains three additional heterodimers, namely VLA-3, VLA-4, and VLA-5. These have been immunopurified and the N-terminal amino acid sequence for each of the VLA α subunits has been determined. The monoclonal antibody recognizing VLA-4 is also disclosed.

DETAILED DESCRIPTION OF THE INVENTION

In addition to the known VLA proteins, VLA-1 and VLA-2, which have been primarily used in correlation with studies on T cells, it has now been found that the VLA β protein subunit is expressed by nearly all human tissues and cell types and that three additional VLA proteins exist having a common β subunit and different but related α subunits in a 1:1 ratio of α:β. The common β subunit has $M_r$ 110,000 (nonreduced) and $M_r$ 130,000 (reduced). The various α subunits for VLA-3, VLA-4 and VLA-5 are identified as $\alpha^3$ with $M_r$ 150,000 (nonreduced), and $M_r$ 135,000 (reduced), $\alpha^4$ with $M_r$ 140,000 (nonreduced) and $M_r$ 150,000 (reduced), and $\alpha^5$ with $M_r$ 150,000 (nonreduced) and $M_r$ 130,000 (reduced), respectively.

Abbreviations used throughout the specification are as follows: mAb, monoclonal antibody; VLA, very late antigen; PS, position-specific; N-CAM, neural cell adhesion molecule.

Monoclonal Antibodies (mABS). The mAbs TS2/7, 12F1, J143, and B-5G10, recognize the $\alpha^1$, $\alpha^2$, $\alpha^3$, and $\alpha^4$ subunits of VLA-1, VLA-2, VLA-3, and VLA-4 respectively. The mAbs 12F1 and J143 are available from K. Pischel and V. Woods, University of California, San Diego, and R. Kantor and L. Old, Sloan-Kettering Institute for Cancer Research, NY, respectively. The mAbs TS2/7 and B-5G10 are available from M. Hemler at Dana Farber Cancer Institute, Boston, Mass. The hybridoma cell line producing monoclonal antibody B-5G10 was deposited with the American Type Culture Collection (ATCC), 2301 Parklawn Drive, Rockville, Md. 20852 on Dec. 17, 1992 and was accorded ATCC Accession Number HB11224. The mAb A-1A5 (M. Hemler, Dana Farber Cancer Institute) specifically recognizes the β subunit common to all VLA proteins (*J. Biol. Chem.* 262:3300, 1987). The mAbs were purified from ascites fluid by 45% ammonium sulfate precipitation and then coupled to CNBr-activated Sepharose 4B (Pharmacia) at 3 mg of mAb per ml of packed beads according to the manufacturer's instructions.

Purification of VLA-1 and VLA-3. Fresh human placenta (from Brigham and Women's Hospital, Boston, Mass.) was extensively washed with ice-cold 0.9% NaCl, freed from amnion and chorion, and blotted dry. The tissue (100 g, wet weight) was diced and homogenized at 0° C. in 5 vol of 10 mM Tris.HCl, pH 7.5/0.15M NaCl/1 mM phenylethylsulfonyl fluoride/1% Nonidet P-40 (buffer A) in a Waring blender (four 30-s bursts at 1-min intervals). The homogenate was centrifuged at 10,000×g for 30 min, and the supernatant was loaded sequentially onto wheatgerm lectin-Sepharose (20 ml) and Ricin-Sepharose (40 ml) columns (Pharmacia). After rinsing with 10 column vol of buffer A, the bound material was eluted with buffer A containing 5% N-acetylglucosamine or 5% galactose, respectively. Combined lectin column eluate was passed through ovalbumin-Sepharose (10 ml) to clear nonspecifically adhering material, sequentially loaded onto TS2/7-Sepharose (5 ml) and J143-Sepharose (1 ml) columns, and then rinsed with 1 column vol of buffer A, 1 column vol of 50 mM NaCl/0.1% deoxycholate, and then 10 column vol of 10 mM Tris.HCl, pH 7.5/0.15M NaCl/ 0.1% deoxycholate. VLA-1 and VLA-3 were eluted from the respective columns with 50 mM diethylamine/0.1% deoxycholate/5% glycerol, pH 11.5, and the pH was immediately neutralized with 0.1 vol of 1M Tris.HCl (pH 6.8).

Purification of VLA-5, VLA-2, and VLA-4. After other VLA structures were depleted from human placenta glycoprotein preparations by TS2/7-, 12F1-, and J143-Sepharose chromatography, VLA-5 was purified from the remaining placenta glycoprotein fraction by β-specific A-1A5-Sepharose chromatography. VLA-2 was purified from 25 g of outdated platelets (from the Dana-Farber Institute blood bank and from the American Red Cross, Boston, Mass.) by 12F1-Sepharose or A-1A5-Sepharose chromatography, and VLA-4 was purified from 100 g of Mot-4 cells by B-5G10-Sepharose (5 ml) using the same procedures as described above.

Gel Separation and Sequence Analyses. Aliquots of column fractions containing up to 1–2 μg of protein were analyzed by NaDodSO$_4$/PAGE on 7% acrylamide gels; this was followed by silver staining to assess yield and purity. Larger amounts of VLA protein (20–50 μg) were run on preparative 5% NaDodSO$_4$/PAGE gels, and aliquots of $^{125}$I-labeled purified VLA proteins were run in adjacent lanes for use as markers to facilitate localization of separated subunits. Nonreducing preparative gels were run for VLA-3 and VLA-5 subunit separations (to prevent comigraton of the α and β subunits), whereas reducing conditions were used for VLA-1, VLA-2, and VLA-4 subunit separation. After preparative NaDodSO$_4$/PAGE, gel slices containing α subunits from each VLA complex were excised and electroeluted as described in *Methods Enzymol.* 91:227 (1983), and about 30–100 pmol of each was sequenced with a gas phase Applied Biosystems (Foster City, Calif.) 470A protein sequencer, carried out at the Harvard Microchemistry Facility (Cambridge, Mass.).

Purification of VLA Proteins. Human placenta extract was enriched for glycoproteins and then sequential immunoaffinity column purification yielded substantial amounts of α and β subunits of VLA-1, VLA-3, and VLA-5, lesser amounts of VLA-2, and no VLA-4. VLA-5 was purified using a β-chain-specific A-1A5-Sepharose column after the other VLA proteins were essentially depleted by TS2/7-, 12F1-, and J143-Sepharose chromatography. The identity of purified placenta VLA-5 was confirmed by testing its reactivity with mouse anti-VLA-5 serum; that serum was prepared against VLA-5 from the cell line K-562, in the absence of any other VLA proteins (*Nature* 326:607, 1987). Whereas only a small amount of VLA-2 was obtained from placenta, larger quantities of VLA-2 could be obtained from platelets, using A-1A-5-Sepharose or 12F1-Sepharose. Platelets express mostly VLA-2, with a variable amount of VLA-5. Following A-1A5-Sepharose immunoaffinity purification and prior to N-terminal sequencing, the VLA-2 α$^2$ subunit was readily separated from any contaminating α$^3$ subunit material by preparative NaDodSO$_4$/PAGE using reducing conditions. Though absent from placenta and platelets, VLA-4 could be purified from the T-lymphoblastoid cell line Molt-4 using B-5G10-Sepharose. In the results obtained, the α$^4$ subunit was preferentially obtained, whereas the β subunit was presumably lost due to dissociation. It is believed that the α$^4$ and β subunits of VLA-4 are easily dissociated.

Comparisons of N-Terminal Amino Acid Sequences. The sequences of the first 14 N-terminal residues of each of the VLA α subunits were obtained (Table 1). They showed substantial homology, especially at positions 1–6 and 10–14. Homology between individual VLA α subunits (summarized in Table 2) ranged from 21% (between α$^1$ and α$^3$) to 75% (between α$^2$ and α$^5$), with an average homology of 42% between any pair of subunits. Allowing for conservative amino acid substitutions homology between different pairs of VLA α subunits is increased to an average of 59% (range, 43–75%). An 80,000 M$_r$ peptide that is often coexpressed with VLA-4 yielded an N-terminal sequence identical to that shown for the α$^4$ subunit. It is believed that this 80,000 M$_r$ peptide is derived from the VLA-α$^4$ subunit by proteolysis.

TABLE 2

Percent homologies among VLA α subunits

| Subunit | VLA-1 | VLA-2 | VLA-3 | VLA-4 | VLA-5 |
|---|---|---|---|---|---|
| | | | % homology | | |
| VLA α$^1$ | — | 46 (62) | 21 (43) | 36 (50) | 38 (54) |
| VLA α$^2$ | 46 (62) | — | 46 (54) | 38 (69) | 75 (75) |
| VLA α$^3$ | 21 (43) | 46 (54) | — | 28 (64) | 46 (54) |
| VLA α$^4$ | 36 (50) | 38 (69) | 28 (64) | — | 46 (69) |
| VLA α$^5$ | 38 (54) | 75 (75) | 46 (54) | 46 (69) | — |

The precent homology is calculated by comparing the 11–14 amino acid residues from each sequece shown in Table 1 (listed at left) to the sequence for each VLA α subunit (listed at top). Percent homologies including conservative amino acid substitutions are shown in parentheses. The following amino acids were considered as conservative substitutions: threonine, serine; phenylalanine, tyrosine; valine, isoleucine, leucine; aspartic acid, glutamic acid; asparagine, glutamine; arginine, lysine; and alanine, glycine.

Based on biochemical studies the VLA-4 structure has been identified as a distinct M$_r$ 150,000/130,000 α$^4$β heterodimer on *T lymphoblastoid* cells of leukemic origin and on peripheral blood T cells. In the absence of a mAb specific for the α$^4$ subunit, VLA-4 is difficult to identify and study because: 1) the α$^4$ subunit could easily be mistaken for α$^2$, α$^3$ or α$^5$, which are all similar in size (M$_r$ 140,000–150,000) when reduced; 2) during analyses of VLA-4 using anti- β reagents, α$^4$ could often be lost due to its apparent weak association with the β subunit; and 3) it has not been feasible to analyze specific cell surface expression of VAL-4.

We have now characterized a mAb which specifically recognizes VLA-4 and thus confirm the existence of VLA-4 heterodimer. Furthermore, we have used this reagent to analyze VLA-4 in terms of: 1) α$^4$β subunit association; 2) cell distribution; 3) changes upon T cell activation; and 4) relation to additional peptides of M$_r$ 80,000 and 70,000.

VLA Protein Purification. Cell membranes were prepared from 100 g of the T leukemic cell line HPB-ALL, solubilized in Nonidet P-40 detergent, and then enriched for glycoproteins using sequential lentil, ricin, and wheat germ lectin affinity columns. The glycoprotein eluate from the lectin columns was applied to a column of the mAb A-1A5 coupled to Sepharaose, and then after washing, the column was eluted with 50 mM diethylamine at pH 11.5. Aliquots of the purified material were analyzed by SDS-PAGE and assessed for yield and purity by the silver-staining technique.

TABLE 1

| Source of subunit: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| | | | | | | N-TERMINAL RESIDUE | | | | | | | | |
| VLA-1 | PHE | (ASN) | VAL | ASP | VAL | LYS | ASP | SER | MET | THR | PHE | (LEU) | GLY | PRO |
| VLA-2 | (PHE) | ASN | LEU | ASP | THR | X | GLU | ASP | ASN | VAL | (PHE) | ARG | (GLY) | (PRO) |
| VLA-3 | (PHE) | ASN | LEU | ASP | THR | ARG | PHE | LEU | VAL | VAL | LYS | GLU | ALA | GLY |
| VLA-4 | TYR | ASN | VAL | ASP | THR | GLU | SER | ALA | LEU | LEU | TYR | GLN | GLY | PRO |
| VLA-5 | PHE | ASN | LEU | ASP | ALA | GLU | ALA | PRO | ALA | VAL | LEU | SER | GLY | PRO |

Production of New Monoclonal Antibodies. New mAb were obtained from BALB/c mice immunized intraperitoneally with immunopurified VLA-4 proteins over a 9-month period. First, A-1A5 antibody complexed with HPB-ALL protein (from 20 g of cells) was injected while absorbed onto *Staphylococcus aureus* Cowan 1 strain, and then after 1.5 months, 2–3 μg of affinity purified VLA-4 proteins in incomplete Freund's adjuvant was injected. After an additional 5 months, *S. aureus* Cowan 1-immune complexes were again injected, followed again after 2 months by purified antigen. Four days later, mouse spleen cells were fused with P3XAg8.653 myeloma cells (*J. Immunol.* 123:1548, 1979) at a ratio of 10:1 according to standard techniques (*Nature* 266:550, 1977) and were divided into 96-well plates in hypoxanthine/aminopterin/thymidine (HAT) medium with normal mouse spleen cells as feeders. Hybridoma supernatants were screened for binding to HPB-ALL cells using $^{125}$I-goat anti-mouse Ig as the second antibody, and positive wells were subcloned by limiting dilution at least two times, prior to the production of ascites in Pristane-primed BALB/c mice. The new mAb B-5G10 and B-5B7 were shown to be IgG1 antibodies by radial immunodiffusion using antisubclass antisera. Monoclonal antibodies to VLA-3 and VLA-5 can be made in similar fashion.

VLA-4 Purification and mAb Production. Since it was believed that the *T lymphoblastoid* cell line HPB-ALL expressed a protein heterodimer named VLA-4, distinct from VLA-1, VLA-2, or VLA-3, this protein was purified from HPB-ALL cells in two steps. First, glycoprotein enrichment was carried out using lectin-Sepharose affinity chromatography, and second, A-1A5-Sepharose chromatography was used to specifically isolate the VLA β protein and any attached α subunits. The immunopurified material contained the VLA β subunit (Mr 130,000), a small amount of material in the position expected for $\alpha^4$ ($M_r$ 150,000), and additional material at $M_r$ 80,000 and 70,000 as shown by silver staining. None of these protein bands appeared in a control experiment.

To obtain an anti-VLA-4 mAb, immunopurified VLA protein was used for mouse immunization, followed by hybridoma production and screening. A mAb (B-5G10) was selected because it bound to the VLA-4 positive cell line HPB-ALL, but not to the VLA-4 negative erythroleukemic cell line K562. At the same time, another mAB (called B-5B7) was selected which bound strongly to both HPB-ALL and K-562 cells.

Immunoprecipitation of VLA-4 by B-5G10. The reactivities of B-5G10 and B-5B7 were further analyzed by immunoprecipitation. Results with B-5G10 were strongly suggestive of an anti-$\alpha^4$ (and thus anti-VLA-4) specificity because: 1) B-5G10 yielded a major $M_r$ 150,000 protein identical in size to that expected for the $\alpha^4$ subunit; 2) B-5G10 was strongly positive on a cell line (HPB-MLT) known to be positive for VLA-4 but very weak or negative for VLA-1, VLA-2, VLA-3, and VLA-5; 3) B-5G10 did not immunoprecipitate proteins from the VLA-4 negative, VLA-5-positive cell line K-562; and 4) B-5G10 recognized relatively more $\alpha^4$ and less β subunit than was recognized by either mAb A-1A5, or B-5B7. In fact, the latter mAB (B-5B7) recognized mostly β, with little or no $\alpha^4$ present. Consistent with β specificity, both B-5B7 and A-1A5 immunoprecipitated VLA β protein from K562. The wide variation in relative levels of $\alpha^4$ and β indicate that 1) the $\alpha^4$ and β subunits of VLA-4 easily dissociated and dissociation is induced by some antibodies (B-5G10, B-5B7) more readily than others (A-1A5). We have found that $\alpha^4$ β association can be more readily maintained if the pH is kept near or below 8.0 and/or if 0.3% CHAPS detergent is used instead of 1% Nonidet P-40.

In addition to $\alpha^4$ and variably associated β subunit, B-5G10 immunopreciptates also often contained a prominent protein of $M_r$ 80,000 and a weaker $M_r$ 70,000 peptide. It is believed that these smaller proteins of $M_r$ 70,000, $M_r$ 80,000 are derived from $\alpha^4$ because: 1) they are serologically cross-reactive with $\alpha^4$ but not with the VLA β subunit; 2) their sizes add up to the size of the $M_r$ 150,000 $\alpha^4$ subunit; 3) when present, they are usually coexpressed with $\alpha^4$ of VLA-4 but not with VLA-1, VLA-2, VLA-3, or VLA-5; and 4) the $M_r$ 80,000 peptide has the same $NH_2$-terminal sequences as $\alpha^4$.

It appears that the $M_r$ 80,000 and 70,000 proteins, like $\alpha^4$, can sometimes remain stably associated with the β subunit. For example, the $M_r$ 70,000 protein was observed to directly cross-link with β, and both peptides have appeared variably in immunoprecipitates obtained using anti- and mAb or hetero-sera.

The above described VLA proteins interfere with cell attachment mechanisms and thus inhibit cell binding to matrix (or cell connective) proteins such as collagen, fibronectin, and laminin. Thus, these proteins inhibit tumor cell metastasis and interfere with immune cell function. Detection of one or more of these proteins in a cell sample will enable prediction of attachment capability of cells and the preferred growth medium. The effects of oncogenes on cell attachment can also be determined by comparing the VLA presence in both natural and transformed cells. These proteins may also have application in the assessment of human T-cell function, particularly in response to antigenic and mitogenic stimuli, and in the correlation and assessment of chronic autoimmune diseases. Monoclonal antibodies to these proteins are useful to detect their presence in a sample, which would assist in the evaluation of chronically activated T cells for diagnosis of chronic diseases such as lupus erythmatosus, multiple sclerosis, rheumatoid arthritis and chronic viral and bacterial infections as well as transplantation rejection.

Monoclonal antibodies recognizing VLA-3, VLA-4 and VLA-5 may be utilized in direct or indirect immunofluorescent studies utilizing conventional procedures. For example, 5 μl (100 g) of purified antibody is mixed with a 100 μl cell suspension containing $5\times10^5$ to $1\times10^6$ cells of interest in 100 μl of PBS with 0.2% BSA and 0.1% sodium azide at pH 7.4. After incubation at 4° C. for 30 minutes, the mixture is diluted with about 2 ml of PBS-BSA-azide buffer, centrifuged at 300 xg for 10 minutes at 4° C., and aspirated. After discarding the supernatant, the cell pellet is resuspended in an appropriate volume of PBS-BSA azide buffer for the type of analysis, e.g. flow cytometry or fluorescence microscope, to be employed. For indirect immunofluorescence, the cell pellet is resuspended in about 100 μl PBS-BSA-azide buffer and 50 μl of FTIC conjugated anti-mouse immunoglobulin, diluted to about 20 μg/ml in PBS-BSA-azide buffer, are added. After incubation at 4° C. for 30 minutes, the mixture is diluted, centrifuged and aspirated as described above, and the cell pellet resuspended in PBS-BSA-azide buffer as appropriate to the type of analysis selected.

What is claimed is:

1. An isolated and purified human VLA-4 protein consisting of an $\alpha^4$ subunit and a β subunit.

2. An isolated and purified human VLA-4 protein having an $\alpha^4$ subunit of $M_r$ 140,000 (non-reduced) and 150,000 (reduced) and a β subunit of $M_r$ 110,000 (non-reduced) and $M_r$ 130,000 (reduced) as determined by sodium dodecyl sulfate polyacrylamide gel electrophoresis on 7% acrylamide gels under denaturing conditions.

3. An isolated and purified human $\alpha^4$ subunit having an $M_r$ 140,000 (non-reduced) and 150,000 (reduced) as determined by sodium dodecyl sulfate polyacrylamide gel electrophoresis on 7% acrylamide gels under denaturing conditions.

4. The isolated and purified human VLA-4 protein of claim 1, wherein the $\alpha^4$ subunit has an N-terminal residue of TYR-ASN-VAL-ASP-THR-GLU-SER-ALA-LEU-LEU-TYR-GLN-GLY-PRO.

5. The isolated and purified human $\alpha^4$ subunit of claim 3, wherein the $\alpha^4$ subunit has an N-terminal residue of TYR-ASN-VAL-ASP-THR-GLU-SER-ALA-LEU-LEU-TYR-GLN-GLY-PRO.

6. The isolated and purified human VLA-4 protein of claim 1, which is purified by immunoprecipitation by the monoclonal antibody B-5G10.

7. The isolated and purified human VLA-4 protein of claim 6, wherein the immunoprecipitation is performed at a pH of about 8.0.

8. The isolated and purified human VLA-4 protein of claim 6, wherein the immunoprecipitation is performed at using 0.3% CHAPS detergent.

9. The isolated and purified human VLA-4 protein of claim 8, wherein the immunoprecipitation is performed at a pH of about 8.

10. The monoclonal antibody B-5G10.

11. A monoclonal antibody which specifically binds to the same epitope of the $\alpha^4$ subunit of VLA-4 as $\beta$-5G10.

* * * * *